United States Patent
Gharpurey

(10) Patent No.: US 6,480,405 B2
(45) Date of Patent: Nov. 12, 2002

(54) FULL-WAVE RECTIFIER

(75) Inventor: Ranjit Gharpurey, Plano, TX (US)

(73) Assignee: Texas Instruments Incorporated, Dallas, TX (US)

( * ) Notice: Subject to any disclaimer, the term of this patent is extended or adjusted under 35 U.S.C. 154(b) by 0 days.

(21) Appl. No.: 10/002,020

(22) Filed: Nov. 1, 2001

(65) Prior Publication Data

US 2002/0060919 A1 May 23, 2002

Related U.S. Application Data

(60) Provisional application No. 60/249,592, filed on Nov. 17, 2000.

(51) Int. Cl.[7] .............................................. H02M 7/217
(52) U.S. Cl. ....................................................... 363/127
(58) Field of Search ............................ 363/84, 89, 125, 363/127; 323/312, 315, 316; 327/534, 535, 538

(56) References Cited

U.S. PATENT DOCUMENTS 4,053,796 A * 10/1977 Van De Plassche ......... 307/261
4,158,882 A * 6/1979 Citta ........................... 363/127
4,228,429 A   10/1980 Tsuchiya et al.
4,605,901 A    8/1986 Kobori et al.
4,708,146 A   11/1987 Lane

* cited by examiner

Primary Examiner—Matthew Nguyen
(74) Attorney, Agent, or Firm—April M. Mosby; W. James Brady; Frederick J. Telecky, Jr.

(57) ABSTRACT

A full-wave rectifier circuit (500) includes a cross-coupled differential pair circuit (501) coupled to a bias circuit (510). At least one constant current source (512, 514) couples to the base of each transistor (506, 508) in the cross-coupled pair circuit (501). A differential pair of transistors (502, 504) drive the cross-coupled pair circuit (501). Cross-coupled devices (506, 508) are used as positive feedback to increase gain for small amplitude signals and to degenerate the devices (502, 504) of the full-wave rectifier. Using this design very precise rectification can be achieved even for $\theta_i < V_T$. Specifically, the bias circuit (510) includes a current source which supplies $\alpha$ multiplied by the current supplied by the current source (512, 514) connected to the base of the transistors (506, 508) in the cross-coupled pair circuit (501). By choosing an appropriate value of $\alpha$, a unity magnitude slope close to the origin is achieved.

4 Claims, 2 Drawing Sheets

FULL-WAVE RECTIFIER

This application claims priority under 35 USC §119 (e)(1) of provisional application No. 60/249,592 filed Nov. 17, 2000.

FIELD OF THE INVENTION

The present invention relates to full-wave rectifier circuits, and, more particularly, to a full-wave rectifier having a unity magnitude slope close to the origin.

BACKGROUND OF THE INVENTION

Rectifiers are the fundamental building blocks in DC power supplies of all types and in DC power transmission used by some electric utilities. Specifically, full-wave rectifiers are often used in analog circuits for power detection of a received or transmitted signal. A single-phase full-wave rectifier circuit, shown in FIG. 1a, with the accompanying input and output voltage waveforms (FIGS. 1b and 1c, respectively) includes a center tapped transformer $T_1$ coupled to a pair of diodes D1 and D2, wherein each diode conducts on opposite half-cycles of the input voltage.

As shown in FIG. 1c, while diode D1 conducts the first half-cycle of the input signal shown in FIG. 1b, diode D2 is off. During the second half-cycle, diode D2 conducts while diode D1 is off. The circuit changes a sinusoidal waveform with no dc component (zero average value) to one with a dc component of $2V_{peak}/\pi$, where the root mean square (rms) value of the output is $0.707V_{peak}$. This implementation is not preferred in an integrated circuit (IC) form since it is difficult to implement transformers in an IC. Further the use of diodes as shown has an electrical problem since the stage that drives the diodes can get severely loaded by the diodes and may need to provide high amounts of current.

Another implementation of the single-phase full-wave rectifier circuit, shown in FIG. 2a, may include a differential amplifier pair of transistors in lieu of the diode pair. Differential signals $V_B+V_i$ and $V_B-V_i$ are applied at the base of the two transistors $Q_1$ and $Q_2$, where $V_B$ is the bias voltage and $V_i$ is the input voltage. The full-wave rectified voltage signal $V_o$ is observed at the common emitter nodes of the two devices $Q_1$ and $Q_2$. An approximate transfer characteristic is shown in FIG. 2b. For bipolar devices that follow an exponential $I_c$ vs. $V_{gs}$ relationship, the output voltage $V_o$ is represented by:

$$V_o \alpha \ln(\text{sech}(\theta_i/2V_T))$$

where $V_T$ is the thermal voltage which is equivalent to the Boltzmann constant, k, multiplied by the temperature, T, divided by the charge, q (kT/q).

The current approach suffers from reduced accuracy for small amplitudes of the signal. Specifically, this circuit has a dead zone close to its zero crossing. An ideal transfer function of the full-wave rectifier circuit is shown in FIG. 4a. A practical realizable transfer function of the circuit of FIG. 2a is shown in FIG. 4b. The dead zone near the zero crossing leads to the appearance of an error voltage $e_i$, in response to a sinusoidal input as shown in FIG. 3. The effect of the dead zone is that the DC voltage output, for small amplitude inputs is much smaller compared to the ideal case. Mathematically, the unity magnitude slope for the implementation of FIG. 2a is approached only when $\theta_i \gg V_T$, in which case $\text{sech}(\theta_i/2V_T)\alpha \exp(-|\theta_i|/2V_T)$. Thus, $V_o\alpha -|\theta_i|$, which has a slope of unity magnitude.

The non-unity slope near the zero-crossing causes problems in the rectification of very small signals, where $\theta_i < 2V_T$, as shown in FIGS. 4a, 4b and 4c. The output voltage of the rectifier is very much smaller than the ideal case.

One approach to solve this problem is to use amplification before the rectifier, but this requires increased power dissipation and reduces the upper limit of the dynamic range. The dynamic range is reduced by a factor of the reciprocal of the amplification. Further, the pre-amplifier needs to be linear over the range of input signals applied.

For example, where the amplification is 10 and the signals to be rectified have peak to peak excursions of 0.3 volt, the full-wave rectifier circuit would require 3 volts to operate. This presently is difficult in an IC implementation. Thus, there is a dynamic range tradeoff in which it is possible to rectify a signal from a smaller voltage input but it is not possible for larger voltages.

Thus, a need exists for an accurate full-wave rectification circuit having a unity magnitude slope close to the origin.

SUMMARY OF THE INVENTION

To address the above-discussed deficiencies of the biasing circuitry for single-ended circuits, the present invention teaches a full-wave rectifier having a unity magnitude slope close to the origin. In particular, a full-wave rectifier in accordance with the present invention includes an emitter coupled pair circuit coupled to a bias circuit. At least one constant current source couples to the base of each transistor in the emitter coupled pair circuit. A pair of transistors cross-couple across the emitter coupled pair circuit. These cross-coupled devices are used as positive feedback to increase gain for small amplitude signals and to degenerate the devices of the full-wave rectifier. Using this design very precise rectification can be achieved even for $\theta_i < V_T$.

Specifically, the bias circuit includes a current source which supplies $\alpha$ multiplied by the current supplied by the current source connected to the base of the transistors in the emitter coupled pair circuit. By choosing an appropriate value of $\alpha$, a unity magnitude slope close to the origin is achieved.

BRIEF DESCRIPTION OF THE DRAWINGS

For a more complete understanding of the present invention and the advantages thereof, reference is now made to the following description taken in conjunction with the accompanying drawings in which like reference numbers indicate like features and wherein:

FIG. 2b is the transfer characteristic of the input voltage sequence vs. the output voltage sequence of the circuit shown in FIG. 2a;

FIG. 3 is a diagram of the actual output voltage sequence vs. time for the circuit shown in FIG. 2a;

FIG. 4a is the transfer characteristic of the ideal and actual input voltage sequence vs. output voltage sequence of the circuit shown in FIG. 2a;

FIG. 4b is a diagram of the input voltage sequence vs. time of the circuit shown in FIG. 2a;

FIG. 4c is a diagram of the ideal output voltage sequence vs. time of the circuit shown in FIG. 2a;

DETAILED DESCRIPTION OF PREFERRED EMBODIMENTS

Figure 1A:
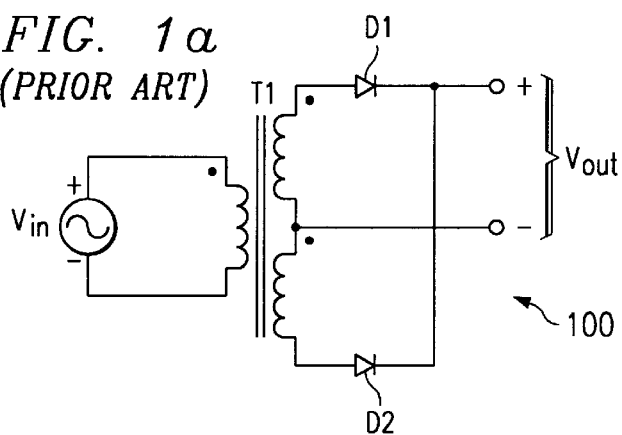
FIG. 1a is a known embodiment of a single-phase full wave rectifier circuit.
Figure 2A:
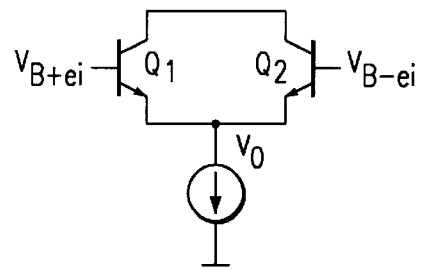
FIG. 2a is another known embodiment of a single-phase full wave rectifier circuit.
Figure 1B:
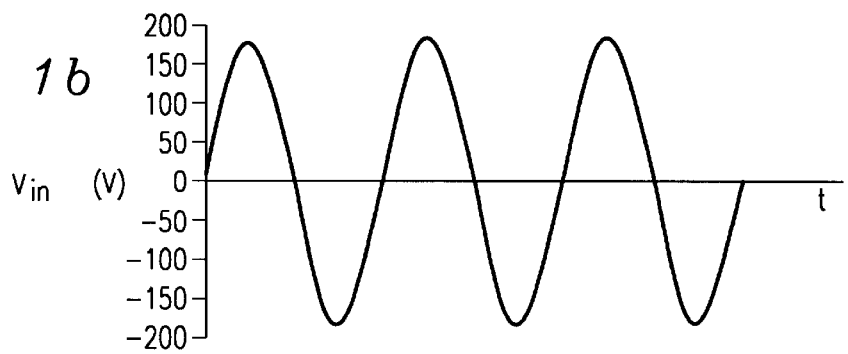
FIG. 1b is a diagram of the input voltage sequence vs. time.
Figure 1C:
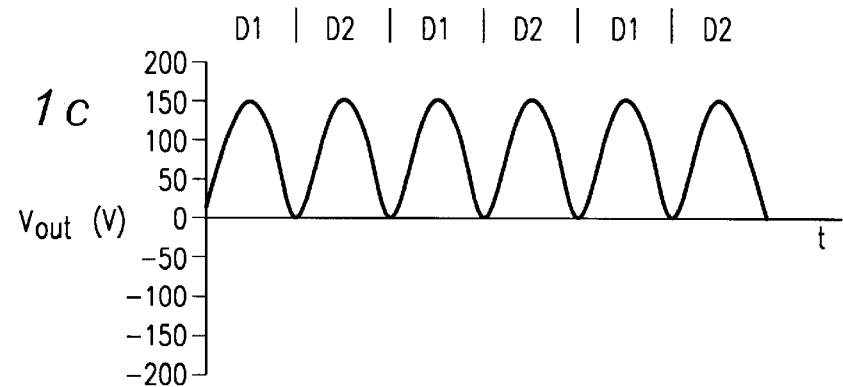
FIG. 1c is a diagram of the ideal output voltage sequence vs. time.
Figure 2B:
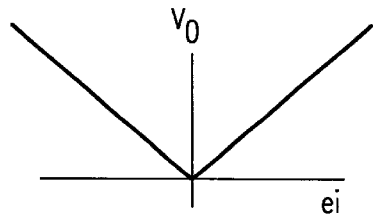
Figure 4A:
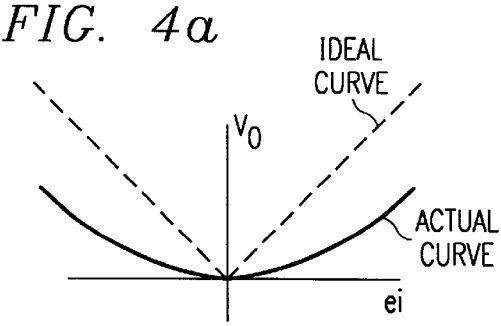
Figure 3:
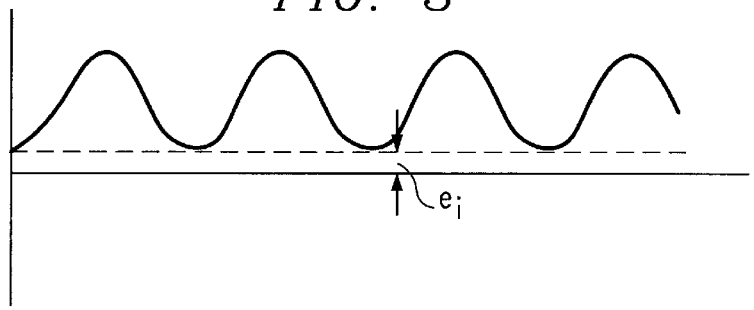
Figure 4B:
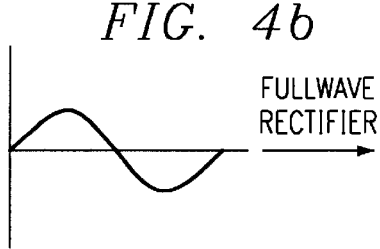
Figure 4C:
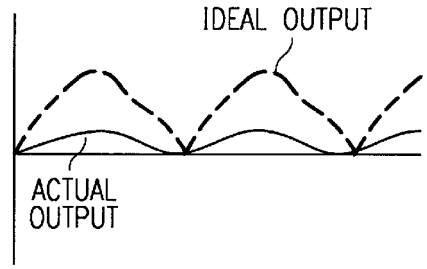
Figure 5:
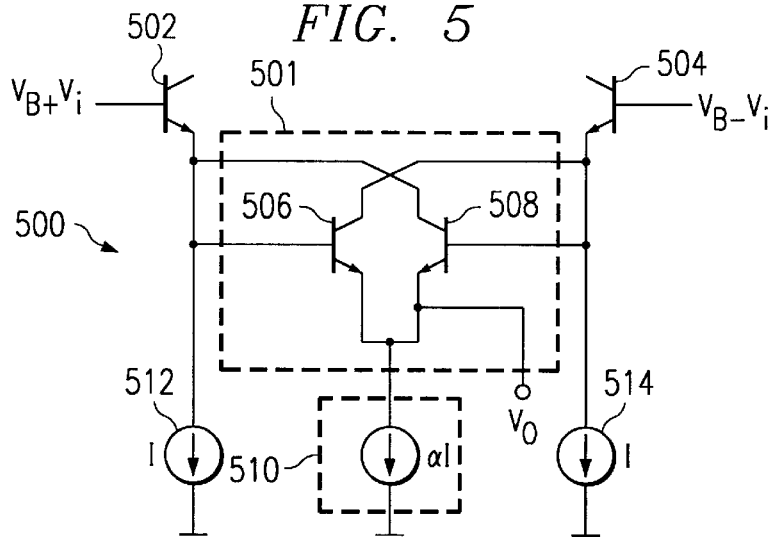
FIG. 5 is an embodiment of a single-phase full wave rectifier circuit in accordance with the present invention.

In FIG. 5, a full-wave rectifier circuit 500 includes cross-coupled differential pair circuit 501 coupled to a bias circuit 510. At least one constant current source 512 and 514 couples to the base of each transistor 506 and 508 in the cross-coupled pair circuit 501. A differential pair of transistors 502 and 504 drive the cross-coupled pair circuit 501. These cross-coupled devices 506 and 508 are used as positive feedback to increase gain for small amplitude signals and to degenerate the devices 502 and 504 of the full-wave rectifier. Using this design very precise rectification can be achieved even for $\theta_i<V_T$.

Specifically, the bias circuit 510 includes a current source which supplies $\alpha$ multiplied by the current supplied by the current sources 512 and 514 connected to the bases of the transistors 506 and 508 in the cross-coupled pair circuit 501. By choosing appropriate values of $\alpha$, a unity magnitude slope close to the origin is achieved.

The positive feedback is used to get a rectified zero voltage output accurately. The cross coupled transistors 506 and 508 effectively represent negative resistance which counters the positive resistance of the differential pair 502 and 504 in the region of the cross-over. The impedance into each of the emitters 502 and 504 is $1/g_m$ which is substantial. The positive feedback tends to alter that positive resistance. It introduces a negative resistance in the emitters of transistors 502 and 504. Looking into the each transistor's 506 and 508 base, a small negative impedance exists which helps to correct for any inaccuracy brought about by the finite impedance of the differential pair 502 and 504.

Figure 6:
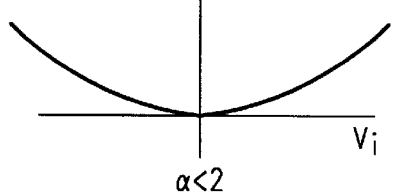
FIG. 6 is the transfer characteristic of the input voltage sequence vs. the output voltage sequence of the circuit shown in FIG. 5 for $\alpha<2$.
Figure 7:
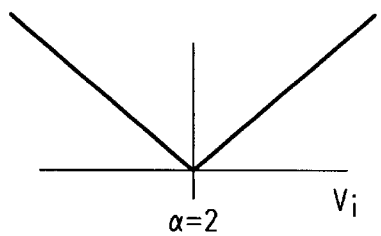
FIG. 7 is the transfer characteristic of the input voltage sequence vs. the output voltage sequence of the circuit shown in FIG. 5 for $\alpha=2$.
Figure 8:
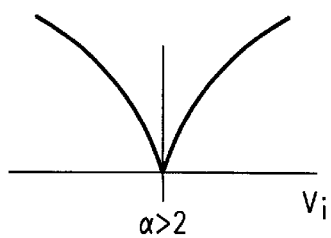
FIG. 8 is the transfer characteristic of the input voltage sequence vs. the output voltage sequence of the circuit shown in FIG. 5 for $\alpha>2$.

If the positive feedback is not implemented, as shown in FIG. 6, the transfer characteristic exhibits a parabolic shape close to zero. After the positive feedback is applied, as shown in FIG. 7, sharpening of the transfer characteristic exists. The parabolic behavior is lost for a certain value of $\alpha$, which represents the ratio of the emitter currents. Setting $\alpha$ approximately equal to 2, gives the optimal transfer curve as shown in FIG. 7. Choosing different values of $\alpha$, different behaviors can be synthesized close to $\theta_i=0$ as shown in FIGS. 6–8.

The reader's attention is directed to all papers and documents which are filed concurrently with this specification and which are open to public inspection with this specification, and the contents of all such papers and documents are incorporated herein by reference.

All the features disclosed in this specification (including any accompany claims, abstract and drawings) may be replaced by alternative features serving the same, equivalent or similar purpose, unless expressly stated otherwise. Thus, unless expressly stated otherwise, each feature disclosed is one example only of a generic series of equivalent or similar features.

The terms and expressions which have been employed in the foregoing specification are used therein as terms of description and not of limitation, and there is no intention in the use of such terms and expressions of excluding equivalents of the features shown and described or portions thereof, it being recognized that the scope of the invention is defined and limited only by the claims which follow.

What is claimed is:

1. A full-wave rectifier circuit, having an input node, an output node, comprising:

(a) a differential cross-coupled pair circuit having a pair of input nodes and an output nodes;

(b) a bias circuit coupled to the output node of the differential cross-coupled pair circuit;

(c) at least one constant current source, each constant current source coupled to one input node of the differential cross-coupled pair; and (d) a differential pair of transistors coupled to drive the differential cross-coupled pair circuit, the first and second transistor each having a respective base, emitter and collector, each emitter coupled to one input node of the differential cross-coupled pair.

2. The full-wave rectifier circuit of claim 1, wherein the differential cross-coupled pair circuit includes a first and a second transistor each having a respective base, emitter and collector, the emitters of the first and second transistor coupled to the output node, the base of each first and second transistor coupled to one of the at least two input nodes.

3. The full-wave rectifier circuit of claim 1, wherein the bias circuit includes a second constant current source supplying a current equivalent to $\alpha$ multiplied by the current supplied by the at least one current source.

4. The full-wave rectifier circuit of claim 1, wherein the base of the first transistor coupled to a voltage source a voltage at $V_B+v_i$, the base of the second transistor coupled to a voltage source a voltage at $V_B-v_i$, where $V_B$ is the bias voltage and $v_i$ is the input voltage.

* * * * *